(12) United States Patent
Kirkwold et al.

(10) Patent No.: US 9,801,964 B2
(45) Date of Patent: Oct. 31, 2017

(54) EVAPORATIVE CYCLES OF CONCENTRATION CONTROL

(71) Applicant: DRI-STEEM Corporation, Eden Prairie, MN (US)

(72) Inventors: Mark Allen Kirkwold, Shakopee, MN (US); Cole K. Farley, Long Lake, MN (US); James M. Lundgreen, Lakeville, MN (US)

(73) Assignee: DRI-STEEM Corporation, Eden Prairie, MN (US)

( * ) Notice: Subject to any disclaimer, the term of this patent is extended or adjusted under 35 U.S.C. 154(b) by 134 days.

(21) Appl. No.: 14/598,863

(22) Filed: Jan. 16, 2015

(65) Prior Publication Data

US 2015/0205305 A1    Jul. 23, 2015

Related U.S. Application Data

(60) Provisional application No. 61/928,740, filed on Jan. 17, 2014, provisional application No. 61/928,764, (Continued)

(51) Int. Cl.
*G05D 9/12* (2006.01)
*A61L 2/10* (2006.01)
(Continued)

(52) U.S. Cl.
CPC ............ *A61L 2/10* (2013.01); *B01F 3/04021* (2013.01); *B01F 3/04078* (2013.01);
(Continued)

(58) Field of Classification Search
CPC ..... G05D 9/12; Y02B 30/545; B01F 3/04078; B01F 3/04085; B01F 3/04021; F28C 3/08;
(Continued)

(56) References Cited

U.S. PATENT DOCUMENTS 2,160,549 A    5/1939  Kurth
6,078,729 A *  6/2000  Kopel ................. F22B 1/284
                                            392/324
(Continued)

FOREIGN PATENT DOCUMENTS

WO    WO 01/79771 A1    10/2001
WO    WO 2007/055838 A2    5/2007

*Primary Examiner* — Shogo Sasaki
(74) *Attorney, Agent, or Firm* — Merchant & Gould P.C.

(57) ABSTRACT

A cycles of concentration (COC) control process and system for an evaporative media cooling system having a water storage tank in fluid communication with a drain valve and a refill valve is disclosed. In one step, the COC control process includes the step of executing a plurality of discrete refill events to maintain a level or volume of water within the storage tank. In another step, the COC control process includes the step of executing a discrete drain event, equaling the volume of a refill event, after a discrete refill event has been executed when necessary to maintain a target cycles of concentration value of the water within the storage tank. In one embodiment, a discrete drain event is executed when the number of refill events is greater than or equals a target cycles of concentration of the water in the storage tank.

7 Claims, 4 Drawing Sheets

Related U.S. Application Data filed on Jan. 17, 2014, provisional application No. 61/928,775, filed on Jan. 17, 2014, provisional application No. 61/928,784, filed on Jan. 17, 2014, provisional application No. 61/928,800, filed on Jan. 17, 2014.

(51) Int. Cl.

| | | |
|---|---|---|
| *F24F 5/00* | (2006.01) | |
| *B01F 3/04* | (2006.01) | |
| *F28C 3/08* | (2006.01) | |
| *F25B 39/02* | (2006.01) | |
| *F25D 7/00* | (2006.01) | |
| *F24F 6/04* | (2006.01) | |
| *F24F 1/00* | (2011.01) | |

(52) U.S. Cl.
CPC ........ *B01F 3/04085* (2013.01); *F24F 5/0035* (2013.01); *F24F 6/043* (2013.01); *F25B 39/02* (2013.01); *F25B 39/028* (2013.01); *F25D 7/00* (2013.01); *F28C 3/08* (2013.01); *G05D 9/12* (2013.01); *F24F 2001/0088* (2013.01); *Y02B 30/545* (2013.01); *Y10T 137/0318* (2015.04); *Y10T 137/7303* (2015.04)

(58) Field of Classification Search
CPC .......... A61L 2/10; F25B 39/028; F25B 39/02; F25D 7/00; F24F 6/043; F24F 2001/0088; F24F 5/0035; Y10T 137/0318; Y10T 137/7303

See application file for complete search history.

(56) References Cited

U.S. PATENT DOCUMENTS

| | | | |
|---|---|---|---|
| 6,338,471 | B1 | 1/2002 | Imsdahl et al. |
| 6,513,339 | B1 | 2/2003 | Kopko |
| 7,165,410 | B2 | 1/2007 | Carr et al. |
| 7,712,300 | B2 | 5/2010 | Bevilacqua et al. |
| 7,765,827 | B2 | 8/2010 | Schlom et al. |
| 7,818,094 | B2 * | 10/2010 | Rambicourt ........... G01N 33/18 417/211.5 |
| 8,496,732 | B2 | 7/2013 | Culp et al. |
| 9,603,957 | B2 | 3/2017 | Kirkwold et al. |
| 2001/0054354 | A1 | 12/2001 | Baudat et al. |
| 2004/0093882 | A1 | 5/2004 | Sangwan et al. |
| 2005/0166615 | A1 * | 8/2005 | Carr ........................ F04B 39/16 62/171 |
| 2007/0101746 | A1 | 5/2007 | Schlom et al. |
| 2011/0030552 | A1 | 2/2011 | Fong et al. |
| 2012/0118148 | A1 | 5/2012 | Culp et al. |
| 2012/0118155 | A1 | 5/2012 | Claridge et al. |
| 2013/0333407 | A1 | 12/2013 | Jarvis |
| 2014/0190198 | A1 | 7/2014 | Slessman et al. |
| 2015/0204552 | A1 | 7/2015 | Kirkwold et al. |
| 2015/0204553 | A1 | 7/2015 | Kirkwold et al. |
| 2015/0204554 | A1 | 7/2015 | Farley et al. |
| 2015/0204588 | A1 | 7/2015 | Lundgreen et al. |
| 2015/0260419 | A1 | 9/2015 | Muenzberg et al. |

* cited by examiner

EVAPORATIVE CYCLES OF CONCENTRATION CONTROL

CROSS-REFERENCE TO RELATED APPLICATIONS

This application claims priority to U.S. Application Ser. No. 61/928,740, filed on Jan. 17, 2014, entitled "Evaporative Cycles of Concentration Control," the entirety of which is incorporated by reference herein. This application also claims priority to U.S. Application Ser. No. 61/928,764, filed on Jan. 17, 2014, entitled "Circulation and Drain System," the entirety of which is incorporated by reference herein. This application claims priority to U.S. Application Ser. No. 61/928,775 filed on Jan. 17, 2014, entitled "Staging Control for an Evaporative Media System," the entirety of which is incorporated by reference herein. This application also claims priority to U.S. Application Ser. No. 61/928,784, filed on Jan. 17, 2014, entitled "Staging Control for an Evaporative Media System," the entirety of which is incorporated by reference herein. This application also claims priority to U.S. Application Ser. No. 61/928,800, filed on Jan. 17, 2014, entitled "Staged Dry Out Control for Evaporative Media Systems," the entirety of which is incorporated by reference herein.

BACKGROUND

Evaporative media systems, for example direct evaporative coolers, are frequently used in commercial and industrial HVAC systems, including applications for data centers and power plant turbine inlet cooling. Evaporative media systems consume less energy than conventional cooling equipment and are increasingly being used to supplement and occasionally replace conventional cooling equipment. In operation, evaporative media systems use the enthalpy of vaporization of water as a means to cool and humidify air. Typically, this is accomplished by flowing air directly through a media wetted with water. As air passes through the wetted media, water evaporates by taking energy from the air to vaporize the water. Accordingly, the air temperature exiting the wetted media is reduced and the humidity is increased while the energy or enthalpy of the exiting air remains the same as the entering air. This type of a process is often referred to as adiabatic cooling.

One aspect of evaporative media systems is that the concentration of the impurities in the water (e.g. non-evaporating solids) in the storage tank increases as the water is evaporated by the media. If this concentration gets too high, scale will form. In order to keep scaling from happening, some of the concentrated water will need to be removed (drained) from the unit. As the water is evaporated and drained, it will accordingly need to be replenished. The draining of the water needs to be done such that a given cycles of concentration (COC) is achieved to control the amount of scaling and/or to prevent excessive scaling, but also such that water is not wasted by draining excessive amounts.

Commercial and industrial evaporative coolers used in HVAC systems control the COC have been configured in a variety of ways. One way uses a constant bleed rate of water drained from the unit. The bleed rate must be adjusted to generally match the output of the unit, which varies with the incoming air conditions and cooling demand, thus changing the actual COC maintained. Generally, the bleed rate method either wastes water from high bleed off rates and resulting low COC or causes fouling from insufficient bleed off rates and excessively high COC.

Another way uses drain events that occur at user configurable time intervals. The actual COC of the water is not known and varies because of the varying conditions and cooling demands. Yet another approach uses a conductivity meter to sense water conductivity in the tank. When the water reaches a user configurable threshold a drain event occurs and the unit is refilled. This approach can provide better COC control than some other methods, but does require the use of a conductivity meter in the tank. Additionally, for proper set-up the conductivity of the make-up water should be known. However, maintaining a target COC based on conductivity introduces errors. For example, since minerals in water precipitate as the water concentrates, the conductivity may not increase at the same rate as the COC. Improvements in COC control approaches for wetted media systems are desired.

SUMMARY

A cycles of concentration (COC) control process and system for an evaporative media cooling system having a water storage tank in fluid communication with a drain valve and a refill valve is disclosed. In one step, the COC control process includes the step of executing a plurality of discrete refill events to maintain a level or volume of water within the storage tank. In one aspect, each discrete refill event includes opening and closing the refill valve to add make-up water to the storage tank. In another step, the COC control process includes the step of executing a discrete drain event after a discrete refill event has been executed when necessary to maintain a target cycles of concentration value of the water within the storage tank. In one aspect, each discrete drain event including opening and closing the drain valve to drain water from the storage tank in an amount that is generally equal to the amount of make-up water added by a single discrete refill event. In one embodiment, a discrete drain event is executed for every fixed number of discrete refill events. In one embodiment, a discrete drain event is executed when the number of refill events is greater than or equals a target cycles of concentration of the water in the storage tank.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Figure 1:
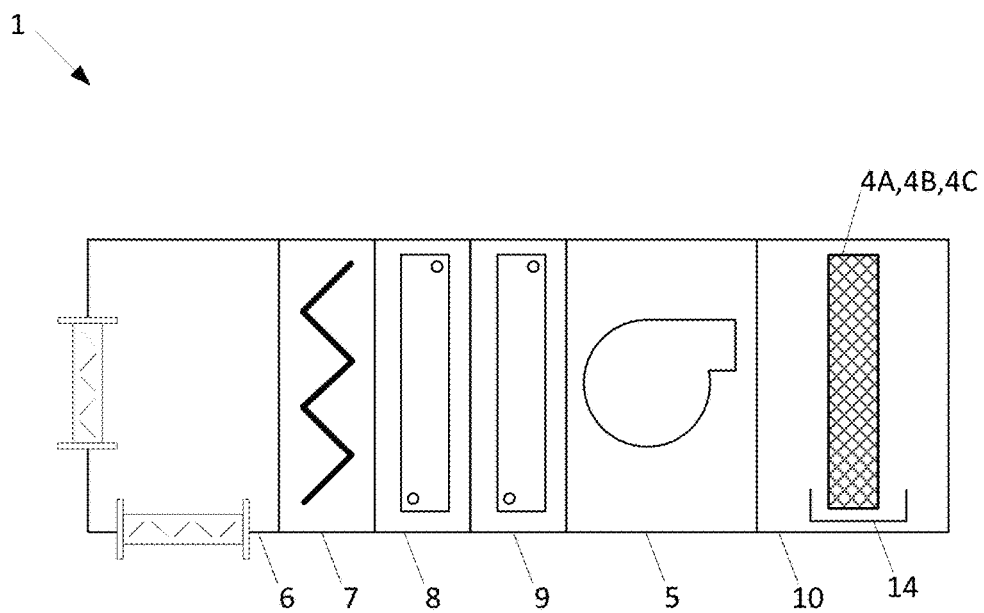
FIG. 1 is a schematic view of an air handling system having features that are examples of aspects in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

General Evaporative Media System Description

Figure 2:
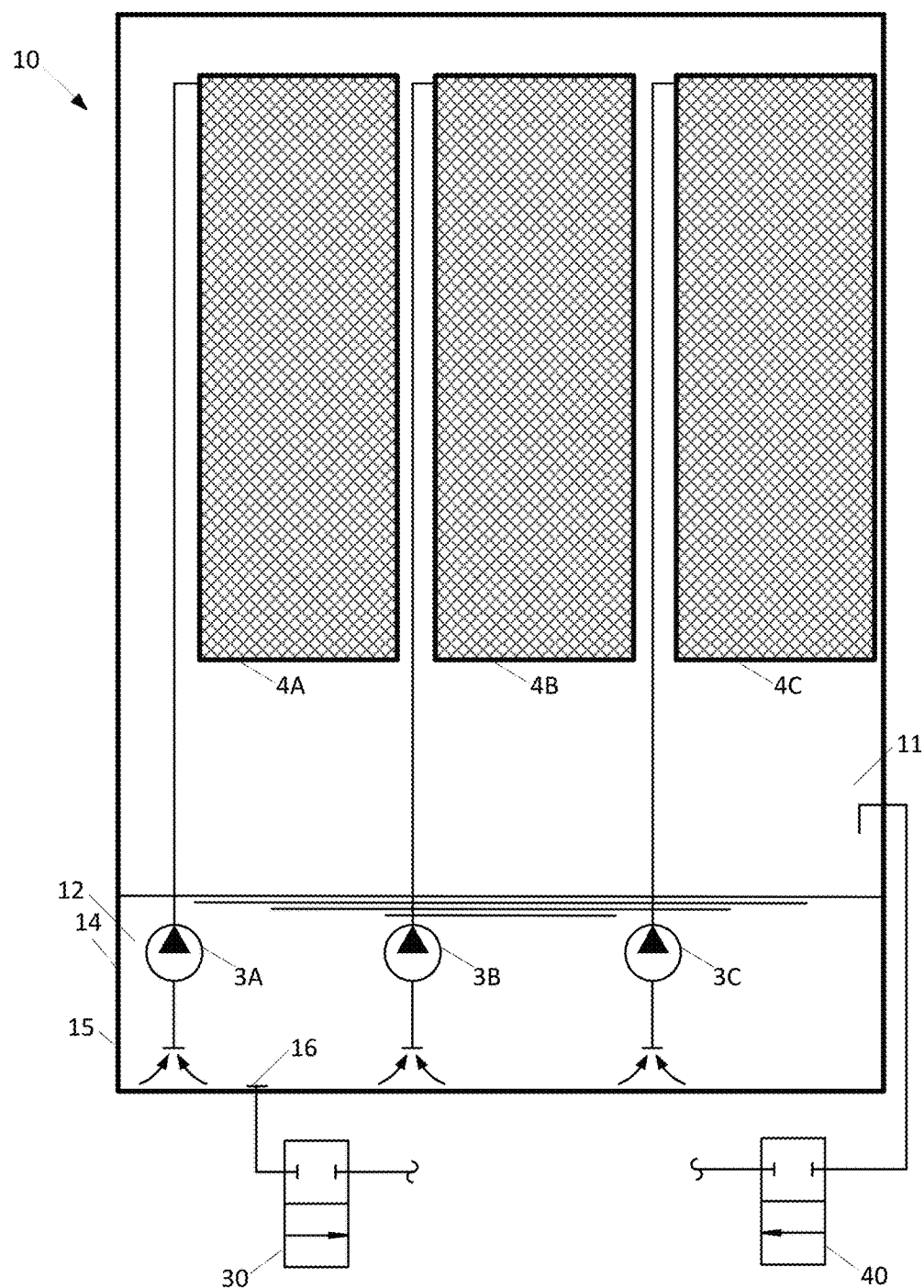
FIG. 2 is a schematic view of an evaporative media system having features that are examples of aspects in accordance with the principles of the present disclosure, the evaporative media system being usable in the air handling system shown in FIG. 1.
Figure 3:
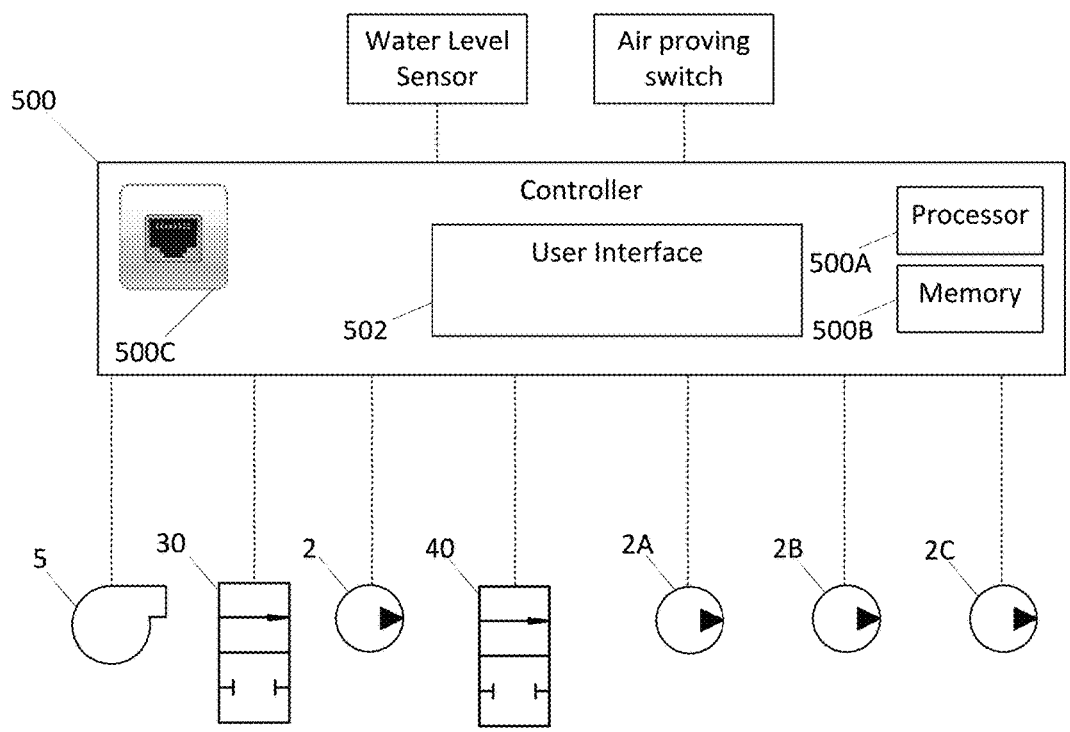
FIG. 3 is a schematic view of a control system usable with the evaporative media system and air handling unit shown in FIG. 1.

Referring to FIG. 1, an air handling system 1 comprising an evaporative media system 10 is shown. FIG. 2 shows the evaporative media system 10 in additional detail. As shown, the air handling unit may be additionally provided with a supply fan 5, a damper section 6, a filter 7, a heating coil 8, and a cooling coil 9. It should be understood that various other components and alternative configurations may be applied to air handling system 1 without departing from the concepts disclosed herein. In operation, the supply fan 5 draws air through the evaporative media system 10 to result in adiabatically cooled air when the evaporative media system 10 is activated.

In one aspect, the evaporative media system 10 includes an evaporator tank 14 having a sidewall 15 and a bottom side 17 that together define an interior volume 11 for holding a fluid 12, such as water. The sidewall 15 may have various cross-sectional shapes as dictated by the requirements of the evaporator and air handling unit, for example square, rectangular, and circular cross-sectional shapes. The bottom side 17 may also be provided with various shapes to accommodate the perimeter defined by the sidewall 15.

The storage tank 14 may be provided with a drain opening 16 located in one of the bottom side 17 and the sidewall 15. In the particular embodiment shown, the drain opening 16 is provided at the bottom side 17 of the tank 14. In one aspect, a drain valve 30 is provided to selectively drain water from the tank 14 while a fill valve 40 is provided to selectively add water to the tank 14. The drain and fill valves 30, 40 may be provided as automatic control valves operated by a controller, such as electronic controller 500 discussed below.

As presented, evaporative media system 10 also includes a plurality of media stages 4A, 4B, 4C through which air is drawn via the operation of fan 5. Although three media stages are shown, it should be appreciated that the evaporative media system 10 may include fewer or more media stages without departing from the concepts disclosed herein. Furthermore, each media stage may include multiple sections of media. As shown, each media section 4A, 4B, 4C is separated from the other by a gap, or alternatively a barrier, to prevent moisture from communicating from one section to the other. This configuration allows for an individual media section to be dry out without being subjected to wicking moisture from an adjacent section.

Each of the media stages 4A, 4B, 4C is shown as being provided with an associated distribution pump 3A, 3B, 3C. While there is a one-to-one relationship shown between the media stages 4A, 4B, 4C and the pumps 3A, 3B, 3C, is should be understood that more than one media stage can be served by a single pump, with or without individual valves, to result in a larger media stage consisting of multiple media sub stages. One suitable pump for pumps 3A, 3B, and 3C is a Little Giant F-Series F10-1200 (manufactured by Franklin Electric of Oklahoma City, Okla.). This type of pump has a wet rotor design without a shaft seal to separate the motor from the pump wherein water circulates around the armature.

In operation, when a pump 3A, 3B, 3C is activated (e.g. turned on or modulated to a speed greater than zero), the associated media stage 4A, 4B, 4C is wetted with fluid 12. When a media stage 4A, 4B, 4C is being actively wetted with water, for example when the associated pump 3A, 3B, 3C is in operation, that media stage 4A, 4B, 4C can be referred to as being activated. Likewise, when a media stage 4A, 4B, 4C is not being actively wetted with water, for example when the associated pump 3A, 3B, 3C is shut off and not in operation, that media stage 4A, 4B, 4C can be referred to as being deactivated.

Control System

Referring to FIG. 2, the evaporative media system may also include an electronic controller 500. The electronic controller 500 is schematically shown as including a processor 500A and a non-transient storage medium or memory 500B, such as RAM, flash drive or a hard drive. Memory 500B is for storing executable code, the operating parameters, and the input from the operator user interface 502 while processor 500A is for executing the code. The electronic controller is also shown as including a transmitting/receiving port 500C, such as an Ethernet port for two-way communication with a WAN/LAN related to an automation system. A user interface 502 may be provided to activate and deactivate the system, allow a user to manipulate certain settings or inputs to the controller 500, and to view information about the system operation.

The electronic controller 500 typically includes at least some form of memory 500B. Examples of memory 500B include computer readable media. Computer readable media includes any available media that can be accessed by the processor 500A. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 500A.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Electronic controller 500 is also shown as having a number of inputs/outputs that may be used for implementing the below described operational modes of the evaporative media system 10 and/or the air handling system 1. For example, electronic controller 500 provides outputs for commanding individual evaporator stage pumps 3A, 3B, 3C, an output for controlling a tank fill valve 40, and an output for controlling a tank drain valve 30. Status inputs can be provided for each of the aforementioned control components as well. Additionally, inputs for entering and leaving air temperature and humidity, outdoor air temperature and humidity, tank water level, tank water temperature (which can serve as a proxy for entering and leaving air wet bulb temperatures), and an airflow switch (or a fan status input signal) may be provided as well. The controller 500 can also include the necessary inputs and outputs for desirable operation of the remaining components of the air handling system 1, for example, inputs and outputs to operate the fan 5, damper section 6, and the coils 8, 9.

In one aspect, the controller 500 may be programmed to execute a cycles of concentration control process whereby the cycles of concentration of the fluid within the tank 14 is maintained at a target value, as explained in the following paragraphs.

Cycles of Concentration Control Process Description

Figure 4:
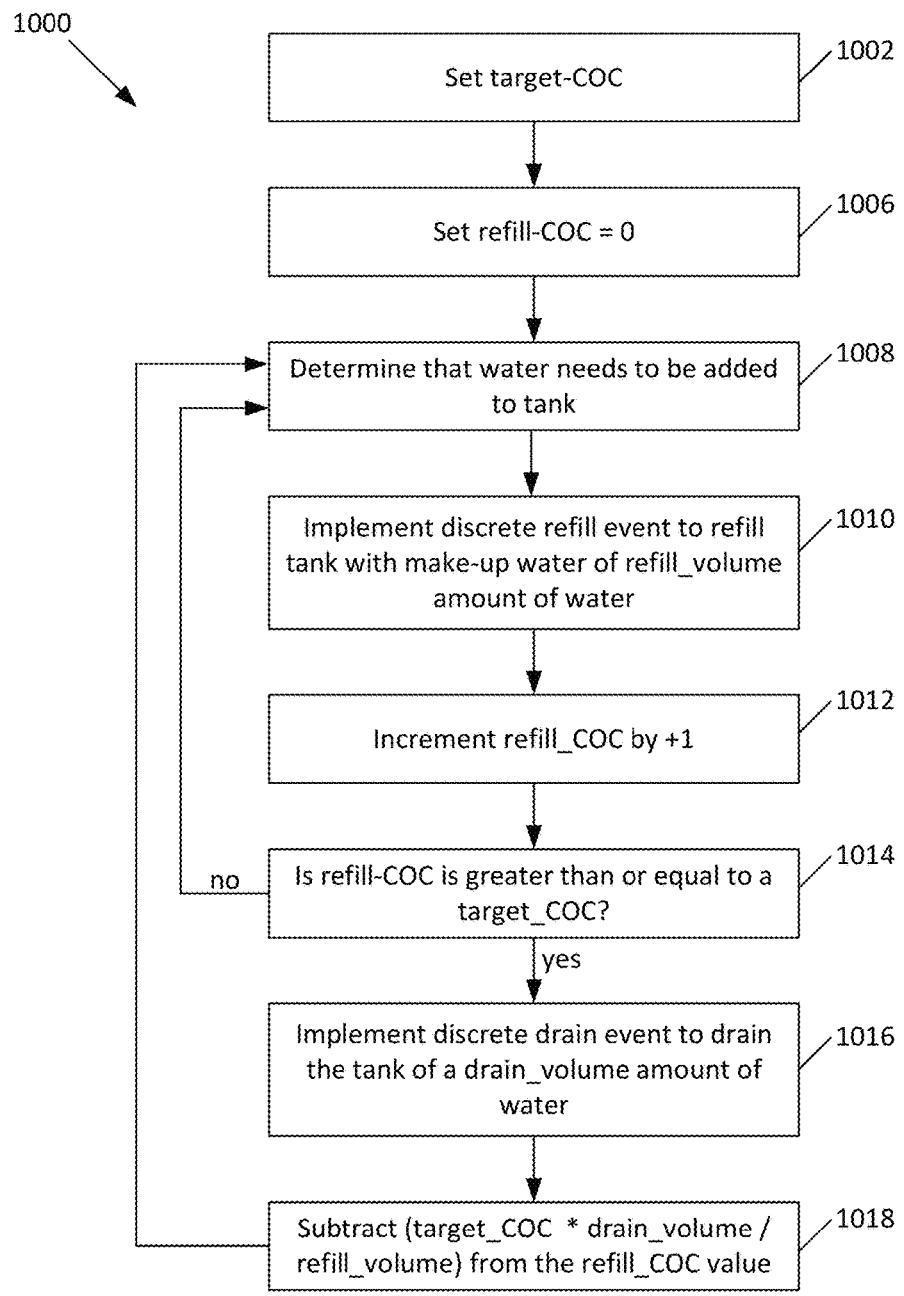
FIG. 4 is a flow diagram for a cycles of concentration control process usable with the air handling system and the evaporative media system shown in FIG. 1, and executable by the control system shown in FIG. 3.

Referring to FIG. 4, an example of a cycles of concentration (COC) control process 1000 in accordance with the disclosure is presented. As used herein, "cycles of concentration" or "COC" is defined as the ratio of the concentration of non-evaporative solids of the water in the storage tank to the concentration of the same solids in the make-up water. Accordingly, when the tank is initially filled with 100% make-up water, the cycles of concentration of the fluid in the tank has a value of 1 (one). Where half of the volume of fluid in the tank is lost due to evaporation, the non-evaporative solids remain in the tank and the cycles of concentration increases to a value of 2 (two). Where water is drained from the tank, the cycles of concentration value does not change, as the non-evaporative solids are generally drained with the water in the same ratio as present in the tank. The disclosed COC control process 1000 operates to maintain a setpoint or predetermined value for the cycles of concentration of the fluid in the storage tank.

It is noted that although the figures diagrammatically show steps in a particular order, the described procedures are not necessarily intended to be limited to being performed in the shown order. Rather at least some of the shown steps may be performed in an overlapping manner, in a different order and/or simultaneously. Also, the process shown in FIG. 4 is exemplary in nature and other steps or combinations of steps may be incorporated or altered without departing from the central concepts disclosed herein.

In a step 1002, a target value ("target_COC") is set for the desired cycles of concentration to be maintained for the fluid within the tank. In one embodiment, the target value is defined as a setpoint in the controller. In one embodiment, the target_COC is calculated from (1) a COC control setpoint that consists of a pair of values: the conductivity of the supply water and the target_COC of the supply water when at the given conductivity and (2) a measurement of the supply water conductivity. As the conductivity of the water varies from the given setpoint, the target COC is adjusted accordingly. For example, if a control setpoint of (400 uS/cm, 4 COC) is given (i.e when the supply water conductivity is 400 micro-siemens/cm then the target_COC should be 4) and if the supply water running to a given unit at a particular moment in time has a conductivity of one half of that given in the control setpoint (i.e 200 uS/cm), it might be reasonable to set the target_COC to twice that given in the control setpoint (i.e. 8).

The ideal mapping of supply water conductivity to target_COC is a function of how the chemistry of the supply water changes with its conductivity. Accordingly, the use of a conductivity sensor in the incoming water stream enables the system to use conductivity as a proxy for such water chemistry changes. Changes in water chemistry over time can be caused by a variety of reasons, for example, mountain run off water. If the water becomes cleaner, the COC target can be raised and vice versa if the water becomes less clean. The controller monitors this conductivity and changes the COC target proportionally based on the original COC target that was established when the wetted media system was first set up.

In a step 1006, after an initial tank fill or the unit is turned on, a refill value (refill_COC) is set to zero. In a step 1008, a determination is made that the tank needs to be refilled with an amount of make-up water. In one embodiment, this determination is made with the use of a water level sensor or switch, or an array of vertically spaced sensors (e.g. an array of conductivity sensors). At a step 1010, make-up water of a given volume is added to the tank by a discrete refill event. The given volume for each discrete refill event can be established, for example, by directly measuring the water flowing through the refill valve or by maintaining the refill valve in an open position for a predetermined period of time. The refill valve can also be opened for a period of time sufficient to raise the level of the water in the tank by a certain amount, for example to raise the water level back up to the level of a sensor. In a step 1012, the refill_COC is incremented upwards by 1.

At a step 1014, a comparison is made between the refill_COC counter and the target_COC value. If the refill_COC counter is less than the target_COC, the process returns to step 1008, where the system will implement another discrete refill event after determining that water needs to be added to the tank yet again. If the refill_COC is greater than or equal to the target_COC, the process moves to step 1016.

At a step 1016, water is drained from the tank by a discrete drain event that drains a volume of water that is some function of the volume added by a discrete refill event. The volume for each discrete drain event can be established, for example, by directly measuring the water flowing through the drain valve or by maintaining the drain valve in an open position for a predetermined period of time (after first establishing a drain rate). In one embodiment, the drain event can be completed when a certain water level, for example a level identified by a water level sensor, is achieved which would correspond to a specific volume if no or little evaporation is occurring. In the case where the drain time is a significant fraction of the refill interval, the evaporation that is going on while the unit is draining can be compensated for by scaling the amount subtracted from refill_COC by the refill interval minus drain time divided by the refill interval. Where the drain time is equal to or greater than the fill interval, no draining is going on. Rather, the water is just evaporating during the "drain" time.

In a step 1018, the target_COC value times drain volume divided by fill volume is subtracted from the refill_COC counter and the process returns to step 1008, where the system will implement another discrete refill event after determining that water needs to be added to the tank.

Example Operation

In one example of the execution of COC control process 1000, the volume of the tank is 2 units, each discrete refill event is 1 unit, each discrete drain event is 1 unit, the target_COC value is set to 4, and a refill event is triggered when the tank is half full. Where the COC of the water is initially 1 (e.g. after filling the tank with make-up water and before any evaporation), the tank will evaporate water until the tank is half full, at which point the COC of the water will be 2. At step 1008 a determination will be made that the tank needs to be refilled with a discrete refill event whereby the COC will be diluted down to 1.5 (e.g. 1 unit of 1 COC water mixing with 1 unit of 2 COC water) after step 1010. Once a refill event has been executed, the refill_COC counter is incremented upward by 1 (0+1) and will have a value of 1. As the refill_COC counter is less than the target_COC value, the process will loop back to step 1008. This looping will occur until the refill_COC value reaches a value of 4 (which is greater than the target_COC value), at which point, the COC of the fluid in the tank will be 3. Once the refill_COC counter matches the target_COC value, a drain event is executed at step 1016 and the target_COC is subtracted from the refill_COC to result in the refill_COC value being set to 0.5. The process is repeated until 3 refills have been done, at which point the refill_COC value will be 3.5 which will initiate another drain. Thus, as the system runs, a drain event will be initiated after 4 then 3 then 4 then 3, etc, fill events, which averages to 3.5, the target_COC.

As this overall series of steps is repeated wherein a unit of water is evaporated, a unit of water is refilled, and a unit of water is intermittently drained, the COC of the water in the tank will gradually rise until the COC of the fluid in the tank matches the target_COC (at the point after step 1016 is executed and the process returns to step 1008 via step 1018). Once this state has been reached, the COC of the water in the tank will match the target_COC value at steps 1016, 1018 through each subsequent iteration of the process, or until the tank is completely drained and the process starts entirely over. Accordingly, the COC control process provides an effective method for maintaining a desired COC level in a fluid tank.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A cycles of concentration (COC) control process for an evaporative media cooling system having a storage tank in fluid communication with a drain valve and a refill valve, the COC control process including the steps of:

a) initially filling the storage tank with water to a first level, the water containing non-evaporative solids at a first concentration;
b) setting a target cycles of concentration setpoint;
c) setting a refill valve counter value to a zero value;
d) detecting that some of the water has evaporated from the storage tank down to a second level below the first level, wherein the water has an increased non-evaporative solids concentration as compared to the concentration at initial filling of the storage tank;
e) refilling the storage tank back to the first level by executing a discrete refill event thereby reducing the non-evaporative solids concentration of the water in the storage tank, the discrete refill event including opening and closing the refill valve to add make-up water to the storage tank;
f) incrementing upwardly the refill valve counter value by a value of one;
g) repeating steps d) to f) until the refill valve counter value equals or exceeds the target cycles of concentration setpoint;
h) executing a discrete drain event in response to determining that the refill valve counter value is greater than or equal to the target cycles of concentration setpoint, the discrete drain event including opening and closing the drain valve to drain water from the storage tank; and
i) subtracting the target cycles of concentration setpoint from the refill valve counter value upon the occurrence of the drain event and returning to step e).

2. The cycles of concentration (COC) control process of claim 1, wherein:
a. the step of executing a plurality of discrete refill events to maintain a level or volume of water within the storage tank includes sensing a level of water within the storage tank.

3. The cycles of concentration (COC) control process of claim 2, wherein:
a. the step sensing a level of water within the storage tank includes utilizing an array more conductivity sensors.

4. The cycles of concentration (COC) control process of claim 1, wherein:
a. the step of executing a refill event includes opening and closing the refill valve for a predetermined amount of time.

5. The cycles of concentration (COC) control process of claim 4, wherein:
a. the step of executing a discrete drain event includes opening and closing the drain valve for a predetermined amount of time.

6. The cycles of concentration (COC) control process of claim 1, wherein:
a. the step of executing a discrete refill event includes opening and closing the refill valve until the water in the storage tank has reached a predefined level.

7. The cycles of concentration (COC) control process of claim 6, wherein:
a. the step of executing a discrete drain event includes opening and closing the drain valve until the water in the storage tank has reached a predefined level.

* * * * *